United States Patent
Levitt et al.

(10) Patent No.: US 6,286,511 B1
(45) Date of Patent: *Sep. 11, 2001

(54) OPHTHALMIC DRAPE WITH TEAR LINE AND METHOD

(75) Inventors: Yolla B. Levitt, Mendota Heights, MN (US); Dennis L. Baker, Houlton, WI (US); Robert A. Davis, Cottage Grove; Camille M. Hildebrandt, Woodbury, both of MN (US); Mary K. Reed, Brookings, SD (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/541,478

(22) Filed: Mar. 31, 2000

Related U.S. Application Data

(63) Continuation of application No. 09/162,684, filed on Sep. 29, 1999, now Pat. No. 6,105,579, which is a continuation-in-part of application No. 09/016,154, filed on Jan. 30, 1998, now abandoned, which is a continuation-in-part of application No. 08/941,821, filed on Oct. 1, 1997, now abandoned.

(51) Int. Cl.$^7$ .................................................. A61B 19/00
(52) U.S. Cl. ............................................ 128/849; 128/853
(58) Field of Search ..................................... 128/849–856

(56) References Cited

U.S. PATENT DOCUMENTS

| Re. 24,906 | 12/1960 | Ulrich . |
| 1,044,698 | 11/1912 | Sideman . |
| 2,294,593 | 9/1942 | Bailey . |
| 3,030,957 | 4/1962 | Melges . |
| 3,068,863 | 12/1962 | Bowman . |
| 3,154,789 | 11/1964 | Lewis . |
| 3,410,266 | 11/1968 | Krzewinski et al. . |

(List continued on next page.)

FOREIGN PATENT DOCUMENTS

| 63114/90 | 3/1991 | (AU) . |
| 1 187 363 | 5/1985 | (CA) . |
| 2025912 | 3/1991 | (CA) . |
| 89 04 426.6 | 5/1989 | (DE) . |
| 3931803 C1 | 5/1990 | (DE) . |
| 0 166 124 A2 | 1/1986 | (EP) . |
| 0 420 073 A1 | 4/1991 | (EP) . |
| 0 420 073 B1 | 4/1991 | (EP) . |
| 2 128 904 | 10/1972 | (FR) . |
| 2 442 047 | 6/1980 | (FR) . |
| WO 89/05131 | 6/1989 | (WO) . |
| WO 94/24954 | 11/1994 | (WO) . |

*Primary Examiner*—Michael A. Brown
(74) *Attorney, Agent, or Firm*—John A. Burtis

(57) ABSTRACT

An ophthalmic surgical drape and a method of applying the drape to a patient. The ophthalmic surgical drape is made from a sheet having an aperture in the interior of the sheet, and at least two tear lines in the sheet extending from the aperture. The drape also has a field of skin compatible adhesive adjacent the aperture, with the field being traversed by the tear lines so as to divide the field into at least two portions. The drape may be provided in a folded condition in which tearing can be accomplished so as to divide the drape into two sections before the drape is unfolded. Also disclosed are two tear lines disposed along an oblique angle, and a method of applying the drape.

20 Claims, 8 Drawing Sheets

U.S. PATENT DOCUMENTS

| | | |
|---|---|---|
| 3,561,439 | 2/1971 | Bayer . |
| 3,565,067 | 2/1971 | Bayer et al. . |
| 3,667,458 | 6/1972 | Krebs . |
| 3,736,928 | 6/1973 | Andersson et al. . |
| 3,750,664 | 8/1973 | Collins . |
| 3,766,913 | 10/1973 | Balin . |
| 3,797,484 | 3/1974 | Ericson . |
| 3,862,632 | 1/1975 | Hinsch . |
| 3,871,369 | 3/1975 | Krzewinski . |
| 3,923,052 | 12/1975 | Zoephel . |
| 3,930,497 | 1/1976 | Krebs et al. . |
| 4,033,341 | 7/1977 | Scrivens . |
| 4,089,331 | 5/1978 | Hartigan et al. . |
| 4,275,720 | 6/1981 | Wichman . |
| 4,316,456 | 2/1982 | Stoneback . |
| 4,323,062 | 4/1982 | Canty . |
| 4,479,492 | 10/1984 | Singer . |
| 4,711,236 | 12/1987 | Glassman . |
| 4,739,753 | 4/1988 | Brehm . |
| 4,869,271 * 9/1989 | Idris | 128/853 |
| 4,873,997 * 10/1989 | Marshall | 128/849 |
| 4,957,120 * 9/1990 | Grier-Idris | 128/849 |
| 4,966,168 * 10/1990 | Glassman | 128/853 |
| 5,109,873 * 5/1992 | Marshall | 128/853 |
| 5,127,423 | 7/1992 | Draeger . |
| 5,140,996 * 8/1992 | Sommers | 128/853 |
| 5,140,997 | 8/1992 | Glussman . |
| 6,105,579 * 8/2000 | Levitt | 128/853 |

* cited by examiner

OPHTHALMIC DRAPE WITH TEAR LINE AND METHOD

This is a continuation of application Ser. No. 09/162,684 filed Sep. 29, 1999 U.S. Pat. No. 6,105,579, which is a continuation-in-part of application Ser. No. 09/016,154, filed Jan. 30, 1998, abandoned which is a continuation-in-part of application Ser. No. 08/941,821, filed Oct. 1, 1997 abandoned.

BACKGROUND OF THE INVENTION

The invention relates generally to surgical drapes and methods of applying such drapes, and more specifically to ophthalmic drapes having adhesive portions that allow them to be adhered to the skin adjacent the eye and methods of applying such drapes. It is also contemplated that the drape could be used for extremity surgeries, ear, nose or throat procedures, tracheostomy or thyroidectomy, and breast surgeries, among other procedures.

In order to perform surgery on the eye it is frequently desirable to apply a surgical drape to the patient to isolate the eyelashes and eyelids from the surgical site to improve exposure of the eye, and provide a sterile drape surface to reduce the chance of infection. For example, in refractive surgery, draping may be primarily performed to pull eyelids and eyelashes away from the eye, and keep them out of the way of the surgical instruments such as microkeratomes.

One product used for this purpose is the Model 1020 ophthalmic drape commercially available from Minnesota Mining and Manufacturing Company, St. Paul, Minnesota. This drape includes a sheet of material having a generally round aperture roughly in the center. A field of skin compatible adhesive contacts a portion of one side of the sheet adjacent this aperture. This adhesive allows the drape to be adhered around the patient's eye, and the rest of the sheet drapes down over the patient's head, hair and face to provide a sterile surface over these areas.

A difficulty arises in that the eye is a delicate structure and the eyelids are very flexible and not the same size and shape in different individuals. In actual practice, medical practitioners sometimes find it inconvenient to conform the margins of the aperture to the edges of a particular patient's eyelids. When this occurs, one expedient that is known to some practitioners is to cut the drape, either partly or else completely into two sections, typically but not always before applying the drape to the patient. This is done to relieve tension in stretched areas, prevent bunching of the adhesive field, and allow the margin of the aperture to be more closely conformed to the margin of the patient's eye. In addition, cutting the drape before application is the preferred practice of many surgeons in order to facilitate one person applying the drape to the upper eyelid first without adhering the lower portions of the adhesive field to the lower eyelid until ready to do so.

It will be appreciated that this expedient is not without its drawbacks. Making such a cut will require the presence of a sterile scissors or the like. Also, making an appropriate cut is inconvenient to do while attempting to preserve the sterility of the drape.

SUMMARY OF THE INVENTION

This invention provides a ophthalmic surgical drape and a method of draping the eye for ophthalmic surgery that allow the drape to be easily conformed to both lids of the eye by a single person without additional tools. This invention solves the problems discussed above by providing a method of applying an ophthalmic drape so that it can easily be adhered to both the upper and lower margins of the eye without requiring the use of separate instruments for cutting and adjusting. This is accomplished by providing at least two tear lines in the sheet that forms the drape at least in the region adjacent to the aperture that permits access to the eye. The practitioner may then adhere a portion of the margin of the aperture to one of the patient's eyelids, and break as much or as little of the tear lines as necessary to create the needed slack to accurately match the rest of the margin of the aperture to the patient's other eyelid. The drape may be completely divided into two similar halves if such an action makes the practitioner's task in accurate placement of the drape easier.

The invention provides a method of applying an ophthalmic surgical drape to upper and lower eyelids of an eye of a patient. A surgical drape is provided comprising a sheet having a periphery and an aperture spaced from the periphery, and at least two tear lines in the sheet extending substantially from the aperture substantially to the periphery. The drape also has a field of skin compatible adhesive adjacent to the aperture, the field being traversed by each of the tear lines so as to divide the field into at least two portions. The sheet is torn partially or completely along at least one of the tear lines. Depending on the size and shape of that particular patient's eyes, more or less tearing might be needed, or it might be most convenient to tear the drape entirely into two portions. In either case the practitioner can conveniently accomplish the matter without the assistance of another person. The method also includes the step of adhering one of the portions of the field of skin compatible adhesive to one of the eyelids (e.g., the upper eyelid). Preferably, the margin of the aperture is curved so that it approximates the shape of the edges of the eyelids of the open human eye. Finally, the method then includes the step of adhering the other portion of the field of skin compatible adhesive to the other eyelid (e.g., the lower eyelid).

In preferred embodiments, the tear lines extend substantially completely from the aperture to the periphery, which provides the practitioner the greatest flexibility if substantial modifications need to be made to accommodate certain patients. Also, it has been found to be particularly convenient to prepare the aperture with a curved, symmetrical margin, and have the points where the lines of perforations extend from the aperture be on diametrically opposed points along the margin.

The tear lines may conveniently be a line of perforations in the sheet of material, or a scored line, or the sheet of material can be weakened by beat or some other physical process so as to readily permit and correctly propagate the desired tear. As used herein, "tear line" refers to a line along which manual tearing of the sheet is directed by any of these mechanisms.

As used herein, "oval-shaped" refers generally to oval and elliptical shapes, as well as elongated curved openings.

In some preferred embodiments, it is convenient to protect the field of skin compatible adhesive by adhering a release liner to the field. The release liner protects the adhesives during shipping and handling, but are peeled away by the user of the drape just before application to the patient. For the convenience during application, at least one edge of the release liner may extend beyond the edge of the adhesive field to provide a tab suitable for gripping.

Also, in preferred embodiments, the drape is provided in a folded condition, folded so that the tearing can be accomplished so as to divide the drape into two sections, such as two similar halves, before the drape is unfolded.

With this in mind, the invention can therefore be viewed in another manner. It can be thought of as an ophthalmic surgical drape comprising a sheet having a periphery, an aperture spaced from the periphery of the sheet, and a tear line in the sheet extending in opposite directions from the aperture to the periphery of the sheet to divide the sheet into two portions. Although there are two portions to the tear line, co-linear on opposite sides of the aperture, this embodiment is designed to be able to be divided before unfolding and therefore it is convenient to think of there being one tear line in two halves. This ophthalmic surgical drape has a field of skin compatible adhesive adjacent the aperture, the field being traversed by the line of perforations so as to divide the field into two adhesive portions, one on each of the two portions of the sheet. The sheet is folded in the direction perpendicular to the tear line, and also along the tear line such that the sheet can be unfolded over the tear line and the two portions of the sheet separated from one another by grasping them and tearing the sheet along the tear before the sheet is unfolded with respect to any fold that is perpendicular to the tear line.

Yet another embodiment of an ophthalmic surgical drape of the invention generally comprises a sheet having a periphery, an aperture spaced from the periphery of the sheet, with the aperture having opposite sides. In this embodiment, two tear lines extend along the sheet at oblique angles relative to one another substantially from opposite side of the aperture substantially to the periphery of the sheet to divide the sheet into two portions. The drape has a field of skin compatible adhesive adjacent the aperture, with the field being traversed by the tear lines so as to divide the field into two adhesive portions, one on each of the two portions of the sheet.

One feature of the oblique tear line angle embodiment is that the two portions of the sheet are of unequal size. Most preferably, the larger portion constitutes an upper portion that is placed over the patients head and hair, with its adhesive portion affixed to the upper eyelid. The oblique angle (e.g., an included angle between the two tear lines of approximately 100 degrees) is preferably selected so that the larger portion of the sheet completely covers the patient's hair adjacent the forehead and ears. This may reduce the chance of the surgeon's gloves or instruments touching the patient's hair between adjacent drape portions. Surgeons typically work from above the patient's head with the patient's body extending generally away from the surgeon, so the larger portion of the drape of this embodiment also faces the surgeon.

Also, preferably, the oblique tear lines extend from opposite edges of the adhesive field generally adjacent the ends of the long axis of the oval-shaped aperture rather than directly from the ends of the long axis of the aperture. In other words, the oblique tear lines are separated from the oval-shaped aperture by the adhesive field. Relatively short tear lines are provided along the adhesive field in the same direction as the long axis of the aperture between the oblique tear line and the aperture.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION OF PREFERRED EMBODIMENTS

Figure 1:
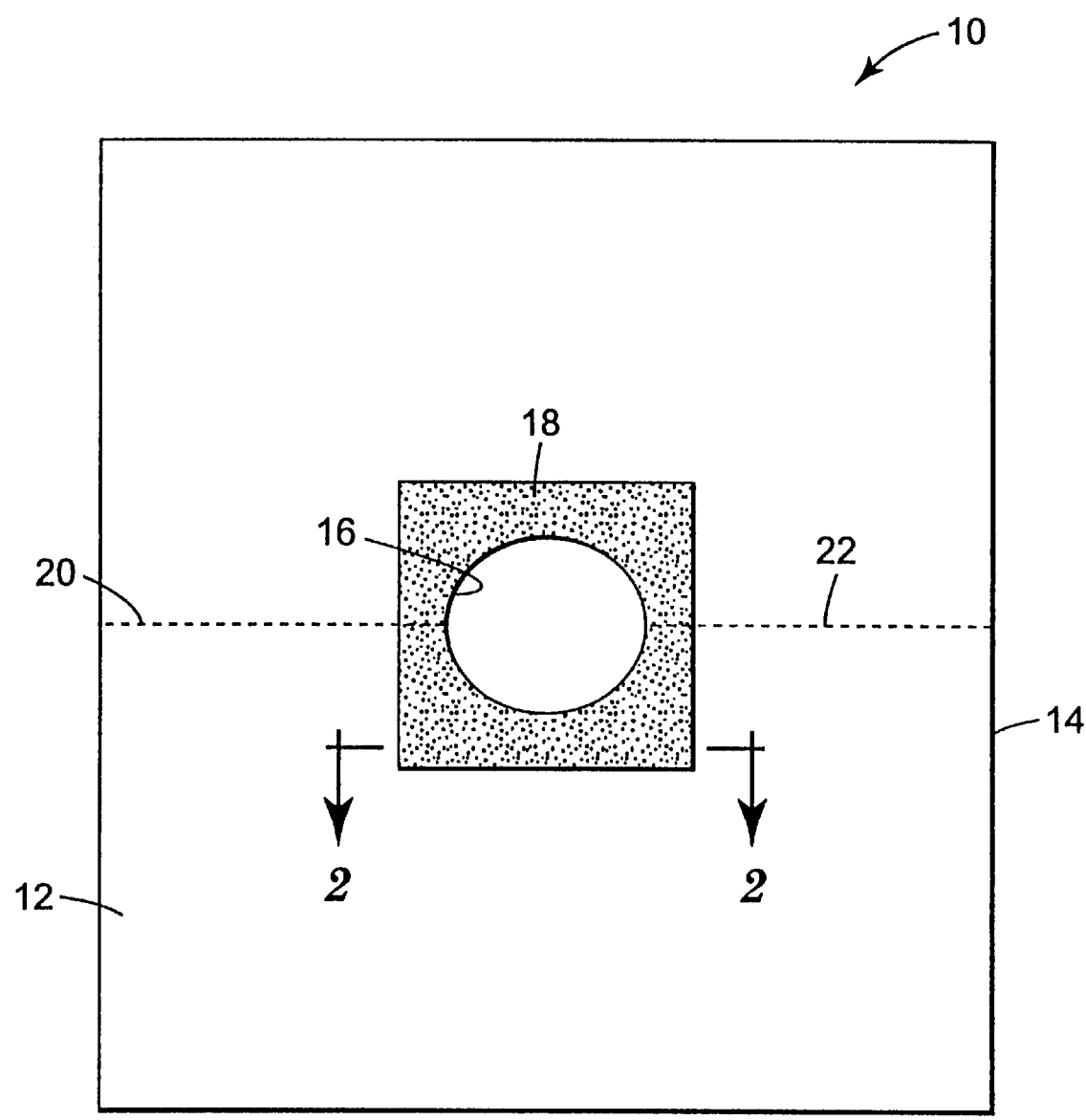
FIG. 1 is a top view of an ophthalmic drape according to a first embodiment of the present invention.

Referring now to FIG. 1, a top view of an ophthalmic surgical drape 10 according to the present invention is illustrated. The drape 10 comprises a sheet 12 (preferably of polymeric film material) having a periphery 14. The sheet 12 has an aperture 16 therein, the aperture being at a position spaced from the periphery 14 of the sheet. A field 18 of skin compatible adhesive contacts a portion of the upper side of the sheet 12 adjacent the aperture 16. Two tear lines 20 and 22 extend away the aperture 16 to the periphery 14. A release liner 24 is removed in this view for clarity, but will be exhibited in FIG. 2.

Figure 2A:
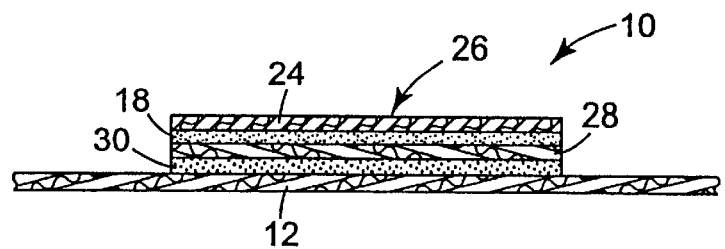
FIG. 2a is a partial cross-section view of the drape of FIG. 1 taken along section lines 2—2.

Referring now to FIG. 2a, a partial cross-section view of the drape of FIG. 1 taken along section lines 2—2 is illustrated. The field of skin compatible adhesive 18 may be applied by pattern coating, or it may be convenient in automated manufacturing to provide it as a subassembly as seen in this Figure. Such a subassembly is prepared as double-stick patch 26 shown adhered to the sheet 12. The patch 26 includes a backing 28 adhered to sheet 12 via adhesive 30. On the other side of backing 28 is the skin-compatible adhesive 18, which will eventually be adhered to the patient. In this view, release liner 24 can be seen protecting skin compatible adhesive 18 before use. Adhesives 18 and 30 may be the same, or may be different adhesives as convenient and compatible with the materials chosen.

Figure 2B:
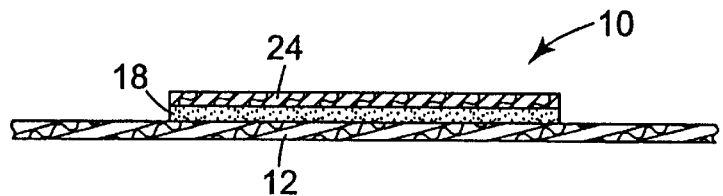
FIG. 2b is a partial cross-section view as in FIG. 2a, of an alternate arrangement.

Referring now to FIG. 2b, a second partial cross-section view of the drape of FIG. 1 taken along section lines 2—2 is illustrated so as to show the application of the field of skin compatible adhesive 18 directly to the sheet 12 as a transfer adhesive. In this case, the release liner 24 is pre-adhered to the field of skin compatible adhesive 18 before the transfer.

Figure 3:
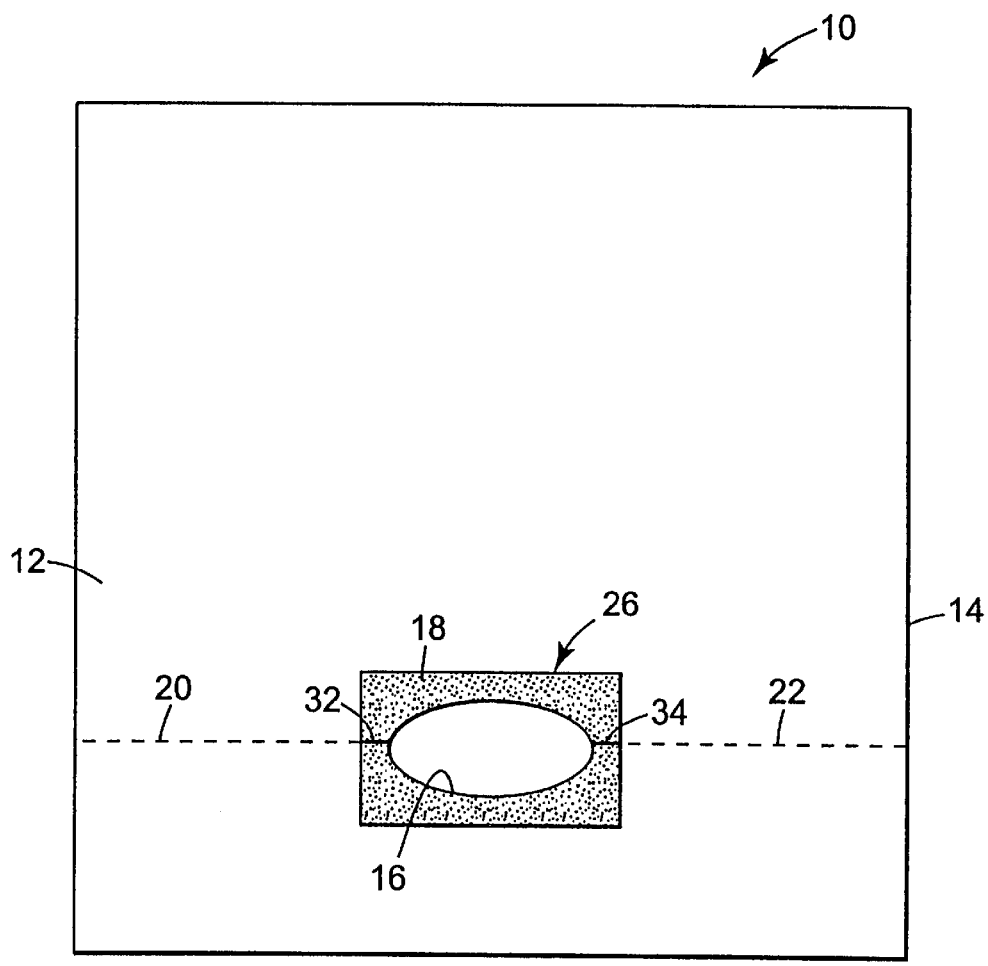
FIG. 3 is a top view of a second embodiment.

Referring now to FIG. 3, a top view of a second embodiment is illustrated. Compared to the embodiment of FIG. 1, this Figure shows that the aperture 16 need not be exactly in the center of sheet 12, and that there is variability in the exact shape of the aperture to account for different types of patients and procedures. It will also be observed that the tear lines 20 and 22 may include slit sections 32 and 34 respectively, which permit the thicker portion where a patch 26 is used to be torn more readily with the fingers.

Figure 4:
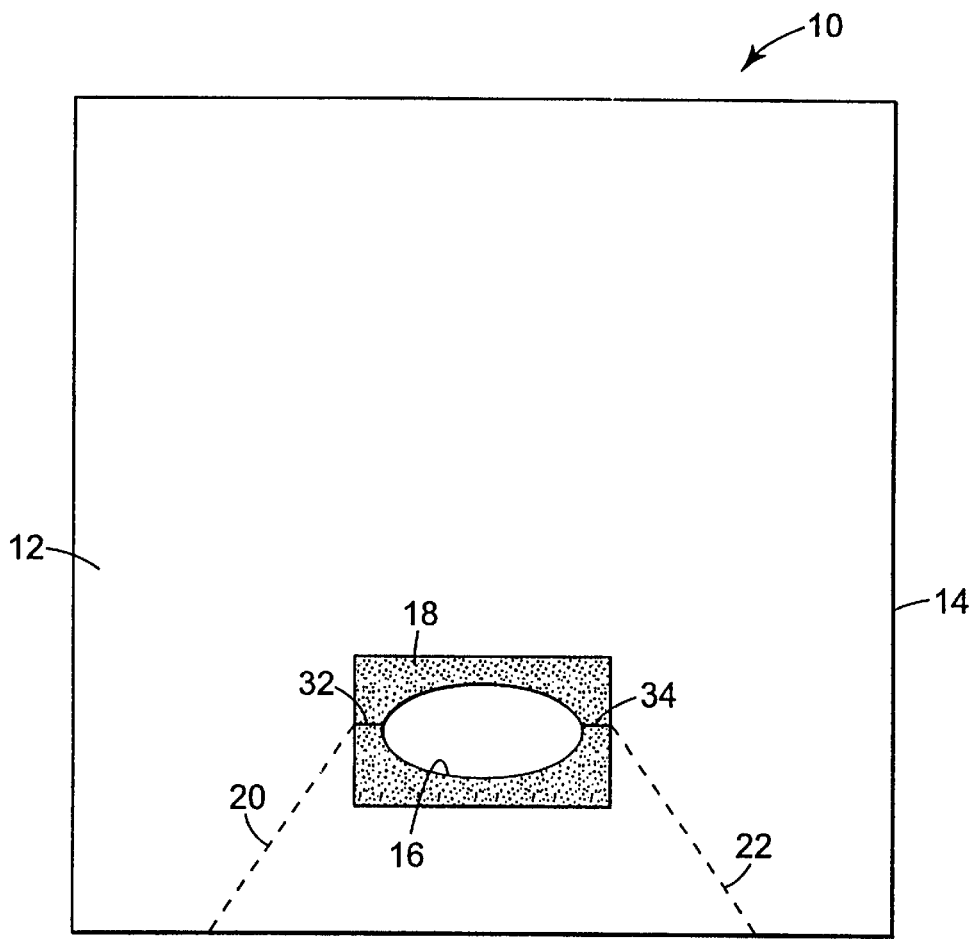
FIG. 4 is a top view of a third embodiment.

Referring now to FIG. 4, a top view of a third embodiment is illustrated.

Compared to the embodiment of FIG. 3, this Figure shows that the tear lines 20 and 22 need not be co-linear, but may instead have an oblique angle to each other. The oblique angle is preferably selected so that the larger portion of the drape, which is used as the upper portion of the drape, completely covers the patient's hair adjacent the forehead and the patient's ears and adjacent hair. For example, the oblique angle, which is defined as the included angle between the two tears lines, may be approximately 100 degrees. It is not a requirement that the lines of perforations 20 and 22 extend all the way to the periphery, although such embodiments are currently considered preferred.

In use, the larger, upper portion of the drape shown in FIG. 4 is placed over the forehead, hair and ears of the patient after affixing the upper portion of the adhesive field to the patient's upper eyelid and pulling the eyelid to obtain appropriate exposure of the eye. The lower portion of the drape may be used to pull the lower eyelid in the direction away from the eye by affixing the lower portion of the adhesive field to the lower eyelid.

The sheet 12 is conveniently fabricated from many sorts of polymeric film, especially polyolefin film. The use of antistatically treated polyethylene film is currently considered preferred. The skin compatible adhesive 18 is conveniently prepared from acrylate adhesive. A discussion of suitable compositions can be found in coassigned U.S. Pat. No. Re. 24,906 to Ulrich, which is hereby incorporated by reference. For example, the acrylate adhesive discussed as Example 5 of that patent is suitable.

Alternatively, for some applications, the sheet 12 could be fabricated from other materials, for example, sheet 12 could be of nonwoven construction including but not limited to melt blown or spun bond webs.

A double-stick adhesive typically comprises adhesive tape with the adhesive coated on both sides and a liner (e.g., a paper or polymeric liner). Pattern coating may involve a printing-type process or die coating. A transfer adhesive typically comprises an adhesive coated on a first liner (e.g., paper or polymer, such as a polyethylene film liner 32 with a silicone release coating, depending on the adhesive) that is removed before or after the transfer adhesive is put to use. A second liner (e.g., paper or polymer, such as a polyethylene film liner 32 with a silicone release coating) may be laminated to the adhesive either before or after the first liner is removed.

The drape is easily prepared from an indefinite length of the sheet material, which forms the main part of the drape. For example, at the first converting station, the indefinite length of sheet material may have adhered to it the transfer adhesive or double-stick patch with its release liner attached as discussed above. At a second converting station, the aperture and the lines of perforations are cut into the sheet and the transfer adhesive or double-stick patch with a rotary die cutter. Finally, a rotary knife cutter sheets off the finished drapes from the indefinite length material, which are then ready to be folded, packaged, and sterilized for the customer.

Figure 5A:
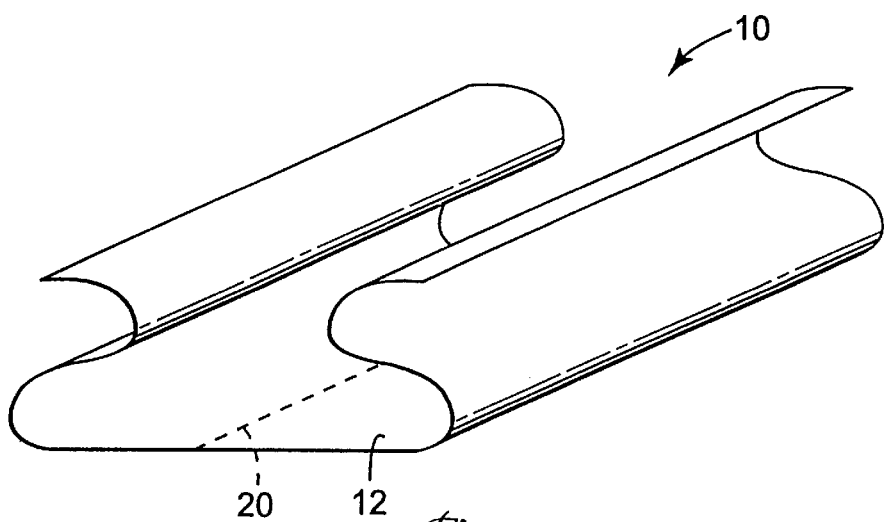
FIGS. 5a–5c are stages along the final folding for the drape of FIG. 1.
Figure 5B:
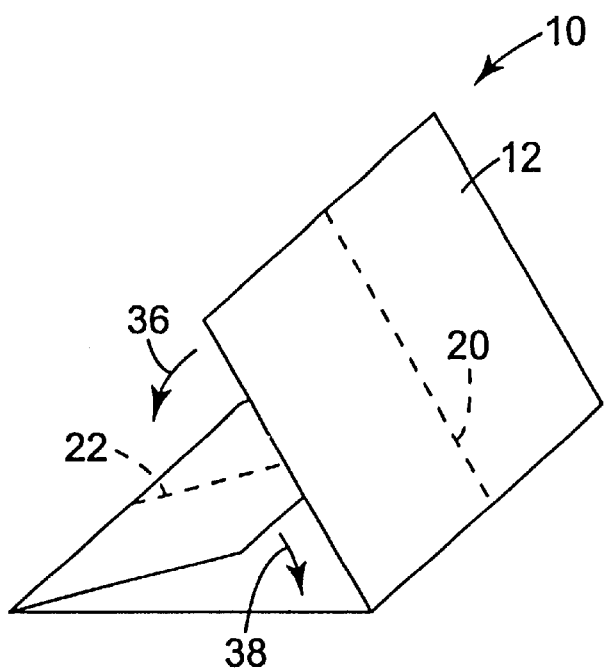
Figure 5C:
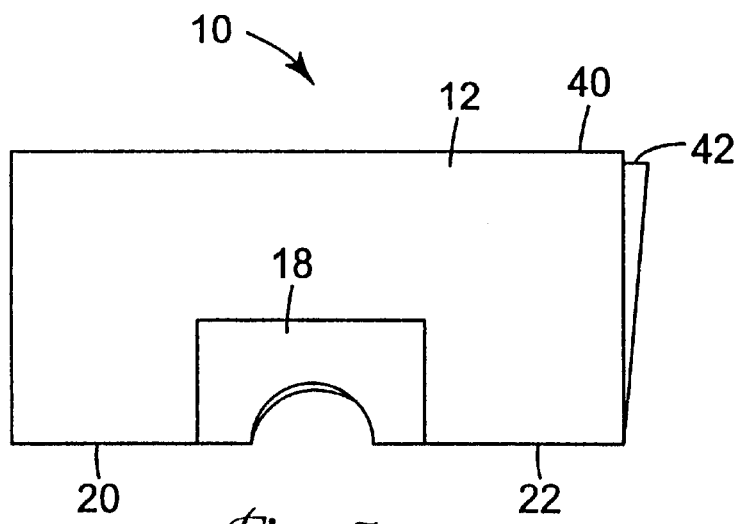
Figure 6:
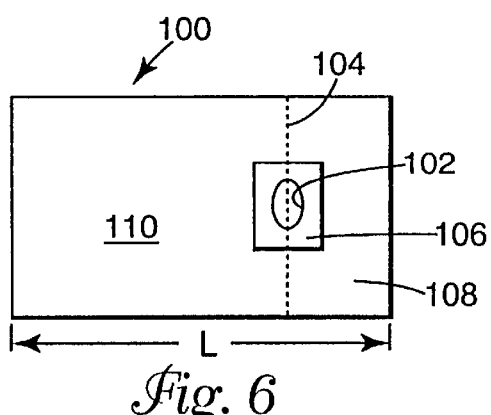
FIGS. 6–13 illustrate another preferred embodiment of the process for folding the drape.

In particular, the embodiment of drape 10 of FIG. 1 can be folded in a way so that the practitioner can conveniently divide the drape into two similar halves with one pull while the drape is still folded if that suits the practitioner's needs. Referring now to FIG. 5a, a finished drape 10 is being folded with two S-folds so that the two co-linear lines of perforations remain in the same plane. A second fold is made as shown by direction arrows 36 and 38 in FIG. 5b. Finally, a third fold is made as shown in FIG. 5c so that all the folded segments of lines of perforations 20 and 22 remain at the vertex of the final fold. This allows the practitioner to take a grip on the drape 10, at for example corners 40 and 42, and separate the drape into to similar halves with one pull.

FIGS. 6–13 show yet another embodiment of the ophthalmic drape of the invention, here designated 100. Drape 100 is similar to the drape 10 shown in FIG. 3. Preferably, drape 100 has a generally rectangular outline, and includes a generally elliptical or elongate eye opening 102, a tear line 104 (which may be formed. for example, by perforations or scoring the drape), and an adhesive field on one surface of the drape in a generally rectangular area surrounding the eye opening. A release liner 106 covers the adhesive field. The tear line 104 preferably extends in a direction defined by the long axis of the elliptical eye opening 102. The preferred tear line 104 is offset rather than dividing the drape in two equal sections. The smaller section 108 of the drape 100 will be referred to as the "short side", and the larger section 110 of the drape will be referred to as the "long side".

Figure 7:
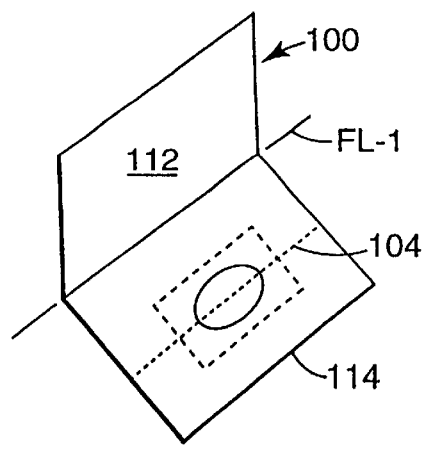
Figure 8:
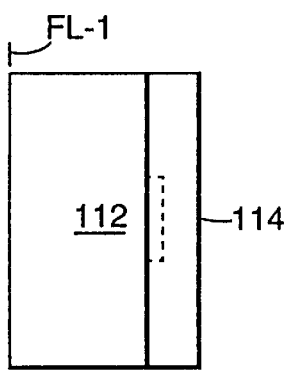

As illustrated in FIGS. 6–13, drape 100 is folded to allow the practitioner to separate the drape 100 into two parts without any prior unfolding. Throughout the preferred folding process illustrated in FIGS. 6–13, the adhesive field and release liner 106 are kept to the outside, i.e., the drape 100 is not folded to cover any portion of the release liner 106. The preferred folding process is a follows:

A. The drape 100 is first folded as illustrated in FIG. 7 along a first fold line FL-1 running through the long side 110 parallel to the tear line 104. The top folded area 112 should completely cover the eye opening 102. If the longer dimension "L" of the rectangular drape 100 is about 27.5 cm, and the tear line 104 is spaced about 7 cm from the first edge 114, then the fold line FL-1 may be spaced about 15 cm from the first edge 112 of the drape 100. The result of this folding step is shown in FIG. 8.

Figure 9:
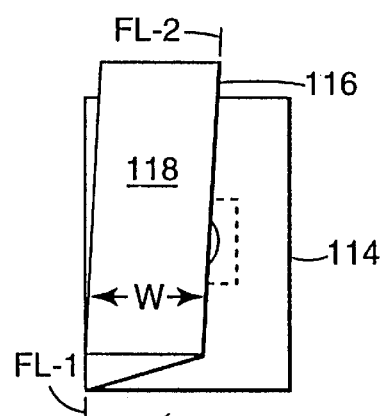
Figure 10:
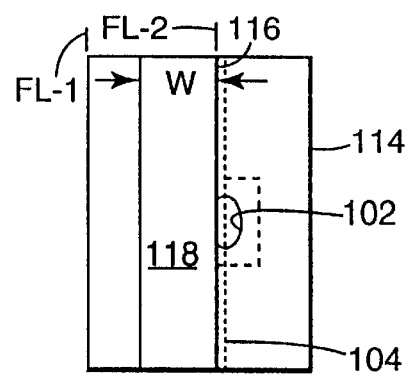

B. The drape is then folded as illustrated in FIGS. 9 and 10 along a second fold line FL-2 in the direction parallel to the tear line 104 in such a manner as to form an "S" or "Z" fold in combination with the first fold. The folded edge 116 of the top folded area 118 should cover less than half of the area of the eye opening 102 and should not cover the tear line 104. For example, if the width "W" of the top folded area 116 may be about 5.8 cm, then the folded edge 116 will be spaced about 1.2 cm from the tear line 104. If the height of the eye opening 102 (i.e., the short dimension of the opening) is about 3.8 cm, this example will result in about 0.7 cm of the eye opening 102 being covered or overlapped by the top folded area 118. It is preferred if this overlapped area is kept less than 1 cm. Alternatively, more than one parallel second fold line could be provided, or this portion of the drape could be "roll" folded.

Figure 11:
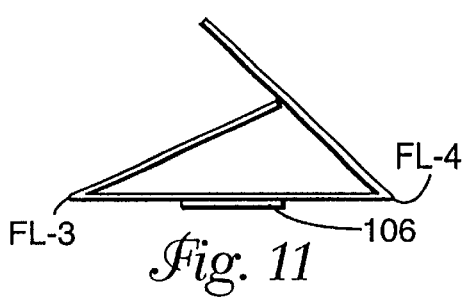
Figure 12:
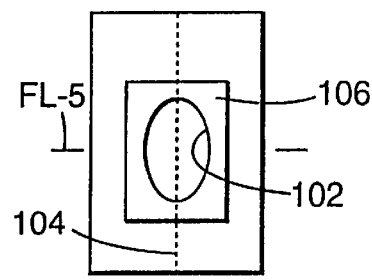

C. The drape is then folded in thirds as illustrated in FIG. 11 along fold lines FL-3 and FL-4 that are generally perpendicular to the tear line 104 and fold lines FL-1 and FL-2. The result of this folding step is shown in FIG. 12.

Figure 13:
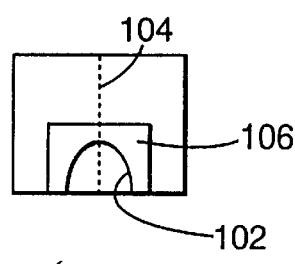

D. The drape is then folded in half along a fold line FL-5 that bisects the eye opening 102 in the direction perpendicular to the tear line 104. The results of this step are shown in FIG. 13. The folded drape shown in FIG. 13 may be separated along the tear line 104 without unfolding the drape.

The preferred folding process set forth in steps A–D above can readily be employed with respect to the drape shown in FIG. 4 with the following understanding: The direction of the inclined tear lines 20 and 22 are not used in the process. In their place, use an imaginary line that bisects the eye opening in a direction parallel to the edge of the drape that intersects that tear lines 20 and 22. With this understanding, the drape with the inclined tear lines 20 and 22 can also be folded in such a manner that it can be separated along the tear lines without unfolding the drape.

Figure 14:
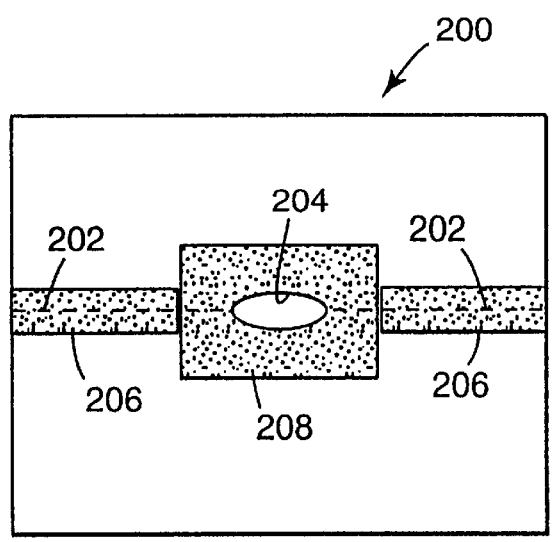
FIGS. 14–21 illustrate additional preferred embodiments of the drape of the invention.

FIG. 14 illustrates another embodiment of the invention in which the drape 200 includes a tear line 202 (e.g., perforations) extending from opposite ends of a generally oval-shaped aperture 204. Adhesive regions 206 and 208 are provided along one surface of the drape 200 adjacent the aperture 204 and tear line.

Figure 15:
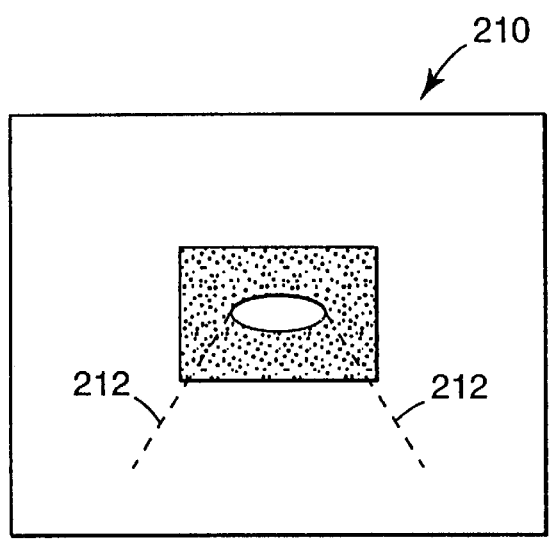

FIG. 15 illustrates a drape 210 of the invention, in which inclined tear lines 212 extend from the ends of the generally oval-shaped aperture 214 only part way to the periphery of the drape 210.

Figure 16:
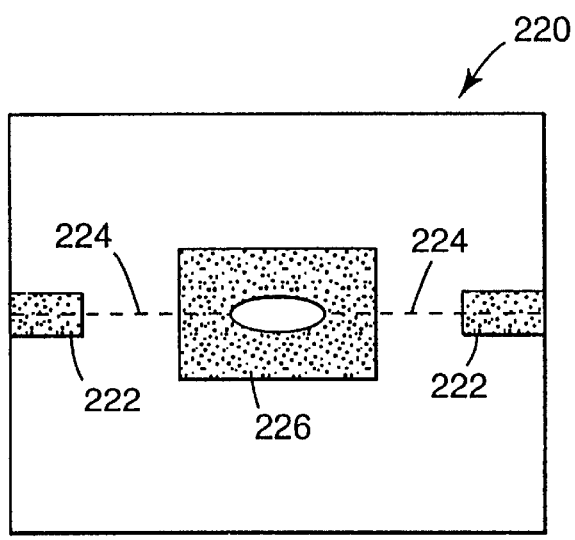

FIG. 16 illustrates a drape 220 similar in some respects to the drape 200 of FIG. 14 except that adhesive regions 222 extend along the tear line 224 inwardly from the peripheral edge of the drape 220 only part way to the central adhesive region 226.

Figure 17:
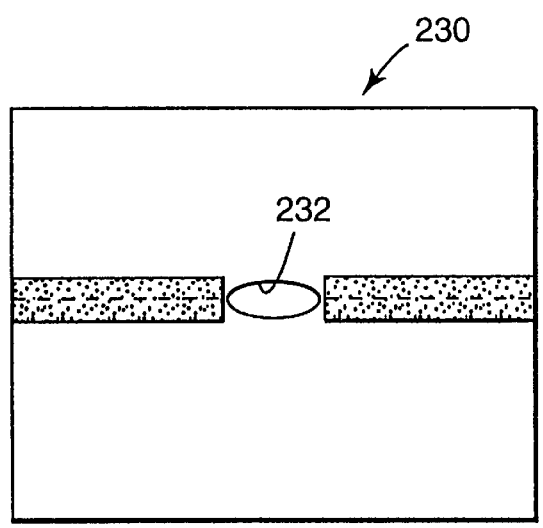

FIG. 17 illustrates a drape 230 similar in some respects to the drape 200 of FIG. 14 except that a central adhesive region surrounding the aperture 232 is not provided in this drape.

Figure 18:
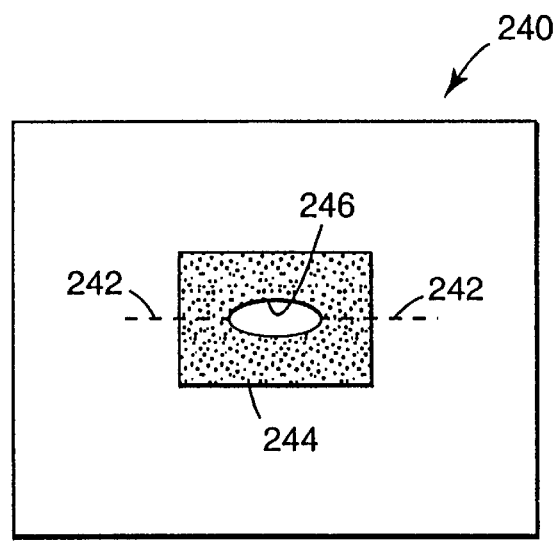

FIG. 18 illustrates a drape 240 in which a tear line 242 extends from both ends of a generally oval-shaped aperture 244 only part way to the edges of the drape. An adhesive region 246 is provided surrounding the aperture 244.

Figure 19:
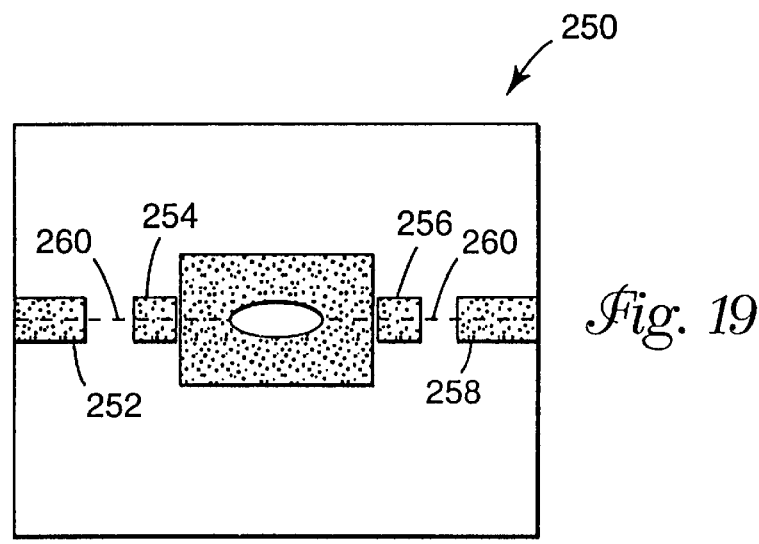

FIG. 19 illustrates a drape 250 similar in many respects to the drape 100 of FIG. 14 except that the adhesive regions 252, 254, 256 and 258 along the tear line 260 are separated by non-adhesive regions.

Figure 20:
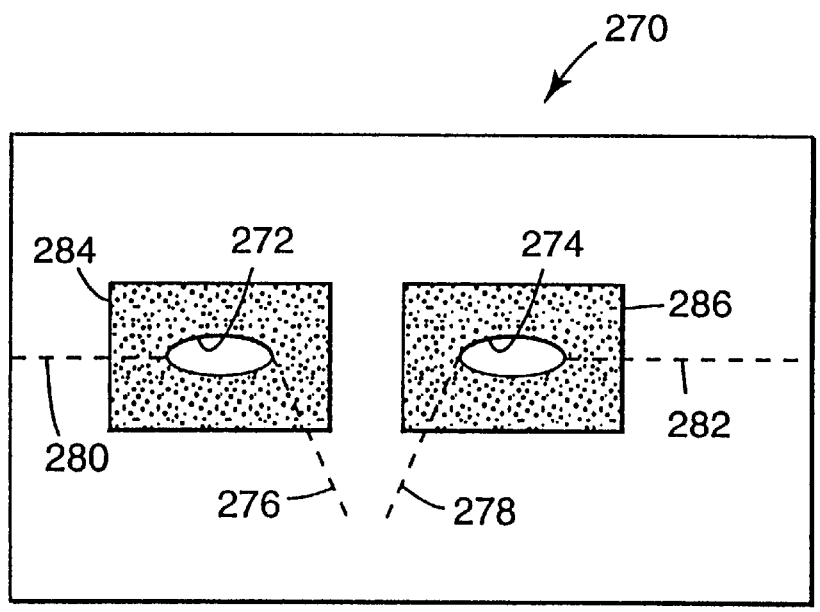

FIG. 20 illustrates a drape 270 which includes two generally oval-shaped apertures 272 and 274, inclined tear lines 276 and 278, laterally-extending tear lines 280 and 282, and adhesive regions 284 and 286 surrounding the apertures 272 and 274.

Figure 21:
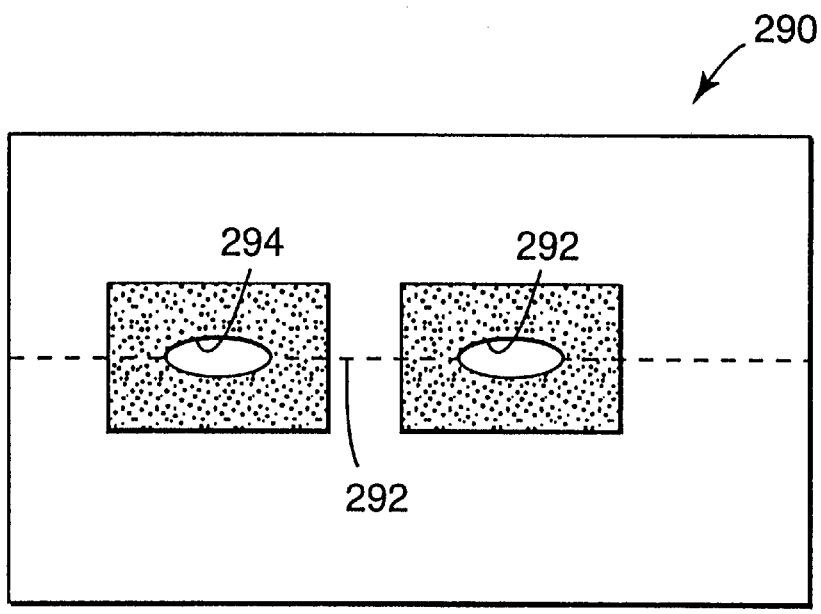

FIG. 21 illustrates a drape 290 similar in many respects to the drape 270 except that the inclined tear lines are replaced by a tear line 292 extending between the apertures 294 and 296.

It is contemplated for some uses that the aperture could be oval, circular, rectangular or any other shape suitable for the use. There can be more than one aperture as illustrated in FIGS. 20 and 21.

U.S. patent application Ser. No. 08/941,820 filed Oct. 1, 1997 by Yolia B. Levitt, Dennis L. Baker, Camille M. Hildebrandt, Mary K. Reed and Robert A. Davis on One-Piece Ophthalmic Drape and Methods is hereby incorporated herein by reference.

As various changes could be made in the above constructions and methods without departing from the scope of the invention as defined in the claims, it is intended that all matter contained in the above description or shown in the accompanying drawings be interpreted as illustrative and not in a limiting sense.

What is claimed is:

1. A method of applying an ophthalmic drape to the upper and lower eyelids of an eye of a patient, the method comprising the following steps:

(a) providing a surgical drape comprising
a sheet having a periphery, an aperture spaced from the periphery of the sheet, and at least two tear lines in the sheet extending substantially from the aperture substantially to the periphery to divide the sheet into two sections; and
a field of skin compatible adhesive adjacent the aperture, the field being traversed by each of the tear lines so as to divide the field into at least two portions, one along each of the two sections of the sheet;

(b) tearing the sheet partially or completely along at least one of the tear lines; and (c) adhering one of the portions of the field of skin compatible adhesive to one of the eyelids; and (d) adhering the other portion of the field of skin compatible adhesive to the other eyelid.

2. The method according to claim 1 wherein each tear line comprises a line of perforations, the step of tearing the sheet partially or completely along at least one of the tear lines comprising tearing the sheet along at least one of the lines of perforations.

3. The method according to claim 2 wherein the lines of perforations extend substantially from the aperture substantially to the periphery, the step of tearing the sheet along at least one of the lines of perforations comprising tearing the sheet along at least one of the tear lines completely between the periphery and the aperture.

4. The method according to claim 2 wherein the aperture has a curved, symmetrical margin, and wherein the points where the lines of perforations extend from the aperture are on diametrically opposed points along the margin.

5. The method according to claim 1 wherein the tear lines are substantially co-linear, the drape being provided in a folded condition folded in the direction perpendicular to the tear lines;

the step of tearing the sheet partially or completely along at least one of the tear lines comprising tearing the drape into two separate sections;
the method further comprising the step of unfolding the drape after the step of tearing the drape into two separate sections; and
the step of adhering the other portion of the field of skin compatible adhesive to the other eyelid including positioning the two separate sections in overlapping relationship.

6. The method according to claim 5 wherein the step (c) of adhering one of the portions of the field of skin compatible adhesive to one of the eyelids is completed before the step of unfolding the drape.

7. The method according to claim 1 wherein the tear lines form an oblique angle;

the step of tearing the sheet partially or completely along at least one of the tear lines comprises tearing the sheet along both tear lines to form two separate sections; and
the step of adhering the other portion of the field of skin compatible adhesive to the other eyelid including positioning the two separate sections in overlapping relationship.

8. The method according to claim 1 wherein a release liner is provided on the field of skin compatible adhesive, the release liner including two tear lines or slits paralleling the tear lines in the sheet to divide the release liner into two sections corresponding to the two portions of the field of skin compatible adhesive;

the method further comprising the following steps:
before the step (c) of adhering one of the portions of the field of skin compatible adhesive to one of the eyelids, removing the corresponding section of the release liner from said one portion of the field of skin compatible adhesive but not the other section of the release liner.

9. An ophthalmic surgical drape comprising:

a sheet having a periphery, an aperture spaced from the periphery of the sheet, and a tear line in the sheet extending in opposite directions from the aperture to the periphery of the sheet to divide the sheet into two portions; and
a field of skin compatible adhesive adjacent the aperture, the field being traversed by the line of perforations so as to divide the field into two adhesive portions, one on each of the two portions of the sheet;
the sheet being folded in the direction perpendicular to the tear line, and also along the tear line such that the sheet can be unfolded over the tear line and the two portions of the sheet separated from one another by grasping them and tearing the sheet along the tear line before the sheet is unfolded with respect to any fold that is perpendicular to the tear line.

10. The ophthalmic surgical drape according to claim 9 wherein the two portions of the sheet are equally sized.

11. The ophthalmic surgical drape according to claim 9 wherein the sheet is formed of polymeric film material.

12. The ophthalmic surgical drape according to claim 9 wherein the tear line comprises a line of perforations.

13. The ophthalmic surgical drape according to claim 12 wherein the line of perforations comprises a multiplicity of slits forming perforations through the sheet.

14. The ophthalmic surgical drape according to claim 13 wherein the line of perforations include two slits extending from the aperture substantially across the field of adhesive.

15. The ophthalmic surgical drape according to claim 9 wherein the drape is folded at least twice in the direction perpendicular to the tear line.

16. The ophthalmic surgical drape according to claim 9 wherein the two portions of the sheet are unequally sized.

17. A combination of the ophthalmic surgical drape according to claim 9 and a release liner releasably affixed to the field of skin compatible adhesive, the release liner being slit or having a tear line to divide the release liner into two pieces corresponding to the two adhesive portions of the drape.

18. An ophthalmic surgical drape comprising:

a sheet having a periphery, an aperture spaced from the periphery of the sheet, the aperture having opposite sides, and two tear lines extending at oblique angles relative to one another substantially from opposite side of the aperture substantially to the periphery of the sheet to divide the sheet into two portions; and a field of skin compatible adhesive adjacent the aperture, the field being traversed by the tear lines so as to divide the field into two adhesive portions, one on each of the two portions of the sheet.

19. The ophthalmic surgical drape according to claim 18 wherein the tear lines each comprise a line of perforations.

20. The ophthalmic surgical drape according to claim 19 wherein the line of perforations comprises a multiplicity of slits forming perforations through the sheet.

* * * * *